United States Patent
Kato et al.

(10) Patent No.: US 12,235,265 B2
(45) Date of Patent: Feb. 25, 2025

(54) IMMUNOCHROMATOGRAPHIC TEST PIECE AND SPECIMEN ADDING DEVICE FOR EXTRACTING AND MEASURING SUGAR CHAIN ANTIGEN, AND IMMUNOCHROMATOGRAPHY METHOD USING SAME

(71) Applicant: Denka Company Limited, Tokyo (JP)

(72) Inventors: Daisuke Kato, Niigata (JP); Tomohiro Hattori, Niigata (JP); Shino Muramatsu, Niigata (JP)

(73) Assignee: Denka Company Limited, Tokyo (JP)

( * ) Notice: Subject to any disclaimer, the term of this patent is extended or adjusted under 35 U.S.C. 154(b) by 718 days.

(21) Appl. No.: 16/308,145

(22) PCT Filed: Jun. 8, 2017

(86) PCT No.: PCT/JP2017/021339
§ 371 (c)(1),
(2) Date: Dec. 7, 2018

(87) PCT Pub. No.: WO2017/213227
PCT Pub. Date: Dec. 14, 2017

(65) Prior Publication Data
US 2019/0145864 A1 May 16, 2019

(30) Foreign Application Priority Data
Jun. 9, 2016 (JP) .................................. 2016-115697

(51) Int. Cl.
*G01N 33/543* (2006.01)
*G01N 1/40* (2006.01)
*G01N 33/569* (2006.01)

(52) U.S. Cl.
CPC ......... *G01N 33/54388* (2021.08); *G01N 1/40* (2013.01); *G01N 33/569* (2013.01); *G01N 2400/00* (2013.01)

(58) Field of Classification Search
CPC .. G01N 1/10; G01N 1/28; G01N 1/40; G01N 2001/4061; G01N 1/4044–4055;
(Continued)

(56) References Cited

U.S. PATENT DOCUMENTS 5,096,837 A * 3/1992 Fan ...................... G01N 33/558
436/514
8,192,926 B2 * 6/2012 Debad .............. G01N 33/56983
435/5

(Continued)

FOREIGN PATENT DOCUMENTS

EP 0280557 A2 * 8/1988 ....... G01N 33/54313
EP 0160240 B1 * 7/1991 ............. G01N 33/84
(Continued)

OTHER PUBLICATIONS

JP2008224543A, translation as retrieved from Espacenet at https://worldwide.espacenet.com/patent/search/family/039843341/publication/JP2008224543A?q=pn%3DJP2008224543A on Apr. 12, 2021, 26 pages total (Year: 2008).*

(Continued)

*Primary Examiner* — Christopher L Chin
*Assistant Examiner* — Christina Lusi
(74) *Attorney, Agent, or Firm* — Foley & Lardner LLP (57) ABSTRACT

The present invention relates to an immunochromatography test method of measuring a sugar chain antigen, which provides an immunochromatographic test piece and a specimen adding device capable of specifically measuring a sugar chain antigen, and an immunochromatography method using the same; wherein after mixing a specimen with a nitrite (Continued)

solution, a step of allowing tartaric acid to come into contact with the mixture, and extracting a sugar chain antigen contained in the specimen is carried out in a filtration step.

6 Claims, 3 Drawing Sheets

(58) Field of Classification Search
CPC ..... G01N 1/4077; G01N 2333/195–2333/365; G01N 33/558; G01N 33/4875; G01N 33/569; G01N 33/54386–54388; G01N 33/54388; G01N 2400/00; G01N 2333/005; G01N 2333/37; G01N 2333/44; G01N 33/5308; G01N 33/54387; G01N 33/54389; Y02A 50/30; B01L 2300/0825
USPC ....... 422/400, 401, 420, 421, 425, 426, 430; 435/287.7, 287.9, 970, 805, 810; 436/169, 170, 514, 518, 530, 810
See application file for complete search history.

(56) References Cited

U.S. PATENT DOCUMENTS

| | | | |
|---|---|---|---|
| 2003/0175362 A1* | 9/2003 | Kross | A61K 45/06 424/718 |
| 2005/0277163 A1* | 12/2005 | Cheng | G01N 33/56944 435/7.32 |
| 2008/0194013 A1 | 8/2008 | Shida et al. | |
| 2008/0206849 A1 | 8/2008 | Zak et al. | |
| 2010/0273177 A1* | 10/2010 | Piasio | G01N 33/56944 435/7.1 |
| 2011/0008909 A1 | 1/2011 | Homrig et al. | |
| 2016/0370368 A1* | 12/2016 | Kato | G01N 33/5306 |
| 2020/0225198 A1* | 7/2020 | Suzuki | G01N 30/48 |

FOREIGN PATENT DOCUMENTS

| | | | | |
|---|---|---|---|---|
| JP | 2003-215126 A | 7/2003 | | |
| JP | 2008-509384 A | 3/2008 | | |
| JP | 2008-128797 A | 6/2008 | | |
| JP | 2008-224543 A | 9/2008 | | |
| JP | 3166728 U | 3/2011 | | |
| JP | 2014-232064 A | 12/2014 | | |
| JP | 2015-034719 A | 2/2015 | | |
| WO | WO 2005/121794 A1 | 12/2005 | | |
| WO | WO-2006079167 A1 * | 8/2006 | ............. | G01N 21/78 |
| WO | WO-2015020210 A1 * | 2/2015 | ....... | G01N 33/54393 |
| WO | WO 2017/213228 A1 | 12/2017 | | |
| WO | WO 2018/168905 A1 | 9/2018 | | |
| WO | WO 2018/168906 A1 | 9/2018 | | |
| WO | WO 2018/168907 A1 | 9/2018 | | |

OTHER PUBLICATIONS

JP2008224543A, translation as retrieved from Google translate at https://patents.google.com/patent/JP2008224543A/en?oq=jp2008224543 on Apr. 12, 2021, 9 pages total (Year: 2008).*
International Search Report dated Sep. 5, 2017, in PCT/JP2017/021339.
Supplementary European Search Report dated Nov. 8, 2019, in EP 17810400.6.

* cited by examiner

IMMUNOCHROMATOGRAPHIC TEST PIECE AND SPECIMEN ADDING DEVICE FOR EXTRACTING AND MEASURING SUGAR CHAIN ANTIGEN, AND IMMUNOCHROMATOGRAPHY METHOD USING SAME

CROSS-REFERENCE TO RELATED APPLICATIONS

This application is the U.S. National Stage of PCT/JP2017/021339, filed Jun. 8, 2017, which claims priority to JP 2016-115697, filed Jun. 9, 2016.

TECHNICAL FIELD

The present invention relates to an immunochromatographic test piece and a specimen adding device for extracting and measuring a sugar chain antigen, which are capable of extracting a sugar chain antigen with nitrous acid on the immunochromatographic test piece, and an immunochromatography method using the same.

BACKGROUND ART

As a method of extracting a sugar chain antigen, a nitrous acid extraction method has been known. This method is mainly used in the extraction of the sugar chain antigen of microorganisms belonging to genus *Streptococcus*, such as group A β-hemolytic streptococcus and intraoral streptococcus.

This nitrous acid extraction method is a method comprising mixing a cell body with an aqueous nitrous acid solution and then exposing a sugar chain antigen. A common nitrous acid extraction method is carried out by mixing a specimen containing microorganisms with a nitrous acid extract, in which nitrous acid has been generated by mixing an aqueous sodium nitrite solution with an acid solution such as acetic acid or hydrochloric acid, and then allowing the microorganisms to react with the nitrous acid for a sufficient period of time. Since the above-described extract is strongly acidic, it is common that, after completion of the reaction, a basic solution such as Tris or sodium hydroxide is added to the extract to neutralize it, and thereafter, analysis is carried out.

On the other hand, a majority of rapid diagnostic agents involving immunochromatography as a principle have been broadly used as a means for promptly and simply measuring viral or bacterial infection and determining a treatment plan therefor.

In the case of such rapid diagnostic agents involving common immunochromatography as a principle, a specimen is suspended in a specimen suspension, and the suspension is then supplied to an immunochromatographic test piece, so that the measurement can be carried out rapidly and simply.

In contrast, for example, when the sugar chain antigen of group A β-hemolytic streptococcus is measured, two solutions, namely, a nitrite solution and an acid solution has previously mixed, immediately before the measurement, to prepare a nitrous acid extract, and the prepared extract is then mixed with a specimen. That is to say, group A β-hemolytic streptococcus is allowed to react with nitrous acid, and thereafter, the reaction mixture is neutralized with a basic aqueous solution. The neutralized extract is supplied to an immunochromatographic test piece.

Since the nitrous acid extract used in this method cannot be preserved for a long period of time, a nitrite solution and an acid solution need to be mixed and prepared immediately before the test. In addition, since this nitrous acid extract has an excessively low pH value, and thus poses an obstacle to an antigen-antibody reaction, it needs to be neutralized to a certain pH value.

However, since the number of steps is increased, such as a step of mixing two solutions and further, a neutralization step, this method requires more reagents than the aforementioned rapid diagnostic agents involving common immunochromatography, and the operation becomes more complicated. Hence, in the case of the existing rapid diagnostic reagents, an immunochromatographic test piece has previously been impregnated with a neutralizing reagent, so that a specimen can be treated by only the operation to mix a nitrite solution with an acid solution. However, since the aforementioned method of using a nitrous acid extract still has more operation steps than the rapid diagnostic reagents involving the conventional immunochromatography method as a principle, this method has been problematic in that inaccurate measurements may be caused by incorrect operations, such as an error in the amount of a solution to be mixed, confusion of a solution to be mixed, and extraction without the mixing of two solutions.

As mentioned above, when operations are carried out by an incorrect method using the rapid diagnostic reagents involving immunochromatography as a principle, incorrect diagnosis and/or treatment are accelerated due to the rapidity and/or simplicity of the method, and thus, the necessary treatment is retarded, thereby causing disadvantage to patients in some cases.

Under such circumstances, a method, in which sodium nitrite and a neutralizing reagent are previously added to an immunochromatographic test piece, so that a nitrous acid extraction treatment can be carried out on the immunochromatographic test piece only by the operation to suspend a specimen in an acid solution such as acetic acid and to supply the suspension to the immunochromatographic test piece, has been reported (Patent Literature 1).

However, sodium nitrite is designated to be a deleterious substance according to the Poisonous and Deleterious Substances Control Law, and belongs to Dangerous Goods Class I according to the Fire Services Act, and is further designated to be a hazardous substance of Enforcement Ordinance Article 2 according to the Water Pollution Prevention Act. Thus, sodium nitrite is a drug that is hard to be handled. Upon the production of the above-described immunochromatographic test piece, a production step of applying a high concentration of aqueous sodium nitrite solution onto a member of the immunochromatographic test piece and then drying it is necessary, but the operation is hazardous.

Hence, a technique of previously impregnating an immunochromatographic test piece not with sodium nitrite but with an acid solution is conceived. However, hydrochloric acid or acetic acid, which is generally used as an acid solution, has provided performance that is significantly inferior to a conventional neutralization method of treating an immunochromatographic test piece with a nitrous acid extract prepared by previously mixing two solutions. In addition, there has also been a method of using an immunochromatographic test piece impregnated with a solid acid reagent such as citric acid, instead of a liquid acid reagent (Patent Literature 2). However, this method has not been suitable for long-term preservation stability, and has been problematic in that a non-specific reaction occurs, etc.

CITATION LIST

Patent Literature

Patent Literature 1: International Publication WO2005/121794
Patent Literature 2: JP Patent Publication (Kohyo) No. 2008-509384 A

SUMMARY OF INVENTION

Technical Problem

It is an object of the present invention to provide: an immunochromatographic test piece and a specimen adding device, which simplify the operation of nitrous acid extraction by performing a step of extracting a sugar chain antigen in a filtration step, in order to more efficiently extract the sugar chain antigen, so that the immunochromatographic test piece and the specimen adding device can specifically measure the sugar chain antigen, precisely and with performance that stands comparison with the conventional nitrous acid extraction method; and an immunochromatography method using the same.

Solution to Problem

The present inventors have conducted intensive studies regarding a method of extracting a sugar chain antigen, using a nitrite and an acid reagent, such that the number of steps necessary for extraction does not increase, when a sugar chain antigen is extracted and is measured using an immunochromatographic test piece. When a test substance is measured using an immunochromatographic test piece, a sample containing a substance to be detected is sometimes filtrated in advance, using a specimen adding device comprising a filter and the like. The present inventors have found that the test substance can be promptly and simply measured by extracting the sugar chain antigen in the aforementioned device. Moreover, in the studies, the present inventors have tried to add an acid reagent in a dry state to a porous material, and then to add the porous material into the device. The present inventors have focused on the fact that since a liquid acid reagent such as hydrochloric acid or acetic acid volatilizes and disappears on a dry porous material, the liquid acid reagent is not fixed on the porous material, and thus, nitrous acid extraction is not sufficiently carried out. Thus, the present inventors have focused a solid acid reagent such as tartaric acid, malic acid, malonic acid, maleic acid or citric acid, and have fixed the acid reagent on a dry porous material without volatilization, so that the present inventors have found that the measurement can be carried out promptly and simply in comparison to a conventional method which comprises treating a specimen with a nitrous acid extract obtained by previously mixing two solutions, namely, sodium nitrite and a liquid acid agent, and then neutralizing the reaction mixture, and further that the measurement can be carried out with performance that stands comparison with the conventional nitrous acid extraction method. Moreover, the present inventors have also found that an antigen is sufficiently extracted, preservation stability is obtained, and a non-specific reaction hardly occurs, by using tartaric acid, among the above-described solid acid reagents, thereby completing the present invention.

Specifically, the present invention provides an immunochromatography test method of measuring a sugar chain antigen, which is characterized in that after mixing a specimen with a nitrite solution, a step of allowing tartaric acid used as a solid acid reagent to come into contact with the mixture is carried out in a filtration step.

The present invention is as follows.

[1] An immunochromatography test method of measuring a sugar chain antigen, wherein after mixing a specimen with a nitrite solution, a step of allowing tartaric acid to come into contact with the mixture, and extracting a sugar chain antigen contained in the specimen is carried out in a filtration step.

[2] The method according to the above [1], wherein the filtration step is carried out in a specimen adding device comprising a porous material impregnated with tartaric acid and a filter.

[3] The method according to the above [1] or [2], wherein a neutralization step after the step of mixing a specimen with a nitrite solution and then allowing tartaric acid to come into contact with the mixture is carried out in a site separated from an immunochromatographic test piece.

[4] The method according to the above [1] or [2], wherein a neutralization step after the step of mixing a specimen with a nitrite solution and then allowing tartaric acid to come into contact with the mixture is carried out on an immunochromatographic test piece.

[5] A method of measuring a sugar chain antigen in a specimen according to the immunochromatography method according to any one of the above [1] to [4], wherein a neutralizing reagent is tris(hydroxymethyl) aminomethane or sodium hydroxide.

[6] A method of measuring a sugar chain antigen in a specimen according to the immunochromatography method according to any one of the above [1] to [5], wherein the sugar chain antigen is the sugar chain antigen of protozoa, fungi, bacteria, mycoplasma, rickettsia, chlamydia, or virus.

[7] A kit comprising an immunochromatographic test piece that measures a sugar chain antigen, and a specimen adding device including a porous material impregnated with tartaric acid, and a filter.

[8] The kit according to the above [7], wherein the specimen adding device further includes a porous material impregnated with a neutralizing reagent.

[9] The kit according to the above [7] or [8], wherein the neutralizing reagent is tris(hydroxymethyl)aminomethane or sodium hydroxide.

[10] The kit according to any one of clams [7] to [9], wherein the sugar chain antigen is the sugar chain antigen of protozoa, fungi, bacteria, mycoplasma, rickettsia, chlamydia, or virus.

The present description includes the contents as disclosed in Japanese Patent Application No. 2016-115697, which is a priority document of the present application.

Advantageous Effects of Invention

By using the immunochromatographic test piece and the specimen adding device of the present invention, the measurement can be carried out promptly and simply in comparison to a conventional method which comprises treating a specimen with a nitrous acid extract obtained by previously mixing two solutions, namely, sodium nitrite and a liquid acid agent, and then neutralizing the reaction mixture, and further, the measurement can be carried out with performance that stands comparison with the conventional nitrous acid extraction method.

DESCRIPTION OF EMBODIMENTS

The present invention relates to a method of simplifying a treatment of extracting a sugar chain antigen with nitrous acid by performing the nitrous acid extraction treatment in a filtration step, so that the sugar chain antigen used as a substance to be detected can be measured promptly and accurately.

Hereinafter, the present invention will be described, showing an example of more specific procedures of the method of the present invention.

(1) A specimen collected from the pharynx, nasal cavity or the like of a patient infected with virus, bacteria, etc. is suspended in a nitrite solution as described later.

(2) This nitrite suspension (sample) is filtrated by a filtration means, and upon the filtration, the sample is treated with an acid reagent to extract a sugar chain antigen.

(3) This filtrate is added dropwise to an immunochromatographic test piece, and the presence or absence of a sugar chain antigen is detected, so that the presence or absence of a substance to be detected in the specimen is measured.

These procedures are given as an example, and thus, the procedures used in the present invention are not limited thereto.

The filtration step of the present invention is carried out in a specimen adding device. The specimen adding device is an accessory separated from an immunochromatographic test piece, and can also be used as a vessel for performing a nitrous acid treatment on the collected specimen. In the nitrous acid treatment of a specimen, which is for use in extracting a sugar chain antigen, the specimen is mixed with nitrite, and an acid reagent is further mixed with the obtained mixture to generate nitrous acid. For this nitrous acid treatment, a nitrite solution may previously have been added into the sample adding device. Otherwise, the specimen may have previously been mixed with a nitrous acid solution, and the mixed solution may be then added into a specimen adding device. Examples of the device include a vial, a syringe, and a tube. Furthermore, the device includes not only a vessel, but also a filtration means for filtering a specimen when the specimen is added and supplied to the immunochromatographic test piece. The specimen adding device includes a vessel portion for accommodating a specimen and a nitrite solution and a portion for adding and supplying the specimen contained in the vessel to the immunochromatographic test piece. The latter portion for adding and supplying the specimen to the immunochromatographic test piece has a portion having a nozzle (opening portion) for discharging the specimen from the vessel, and this portion may also serve as a lid of the vessel portion. The latter portion for adding and supplying the specimen to the immunochromatographic test piece is also referred to as a nozzle portion or a lid portion. Further, when the specimen adding device includes a filtration means, the specimen adding device may be composed of two members, namely, a nozzle portion consisting of a filter housing comprising a filtration filter and a vessel portion, as described below. In this case, the filter housing has an opening portion allowing the specimen to pass through the filter and another opening portion discharging the specimen passing through the filter, and the filter is present between the two opening portions. As a vessel, a syringe capable of allowing a specimen to pass through a filter by applying pressure thereto may be used, for example.

The acid reagent necessary for the nitrous acid treatment may have previously been added to the specimen adding device, or it may also be added to the specimen adding device when the nitrous acid treatment is performed on the specimen.

A solid acid reagent is used as such an acid reagent.

The solid acid reagent used in the present invention is preferably a reagent, which has properties by which it is in a solid state at normal temperature and it does not volatilize at a high temperature, and also it is not colored on the immunochromatographic test piece, and more specifically, a reagent, which has white color in a dry state or is hardly colored by dry heat or oxidation.

From the viewpoint of antigen-extracting ability, if an acid with a higher valence is used, extraction can be performed with a smaller amount of acid. On the other hand, if the valence of an acid is the same, as the acid dissociation constant of the reagent decreases, an antigen can be more efficiently extracted.

Examples of a solid acid reagent having the aforementioned properties may include tartaric acid, malonic acid, malic acid, maleic acid, and citric acid. However, in the present invention, the solid acid reagent, which has all of the above-described properties and also has antigen-extracting ability equivalent to that of a liquid acid reagent, is only tartaric acid.

Tartaric acid is used, such that a porous material is impregnated with the tartaric acid and is then dried. Examples of the porous material that can be used herein include a filter, a glass fiber, and a non-woven fabric, which are commonly used.

In order to impregnate a porous material with tartaric acid, the tartaric acid is once dissolved in a solution, and the obtained solution is then applied to the porous material and is then dried.

The amount of tartaric acid used in the present invention, namely, the amount of tartaric acid impregnated into a porous material is not particularly limited. In general, the amount of tartaric acid is approximately 0.01 μg to 1 mg, and is preferably approximately 0.1 μg to 0.1 mg, with respect to a single immunochromatographic test piece. However, it is preferable to select an optimal amount, in which effects can be obtained depending on the composition of a specimen suspension, the amount added dropwise, etc.

Figure 1:
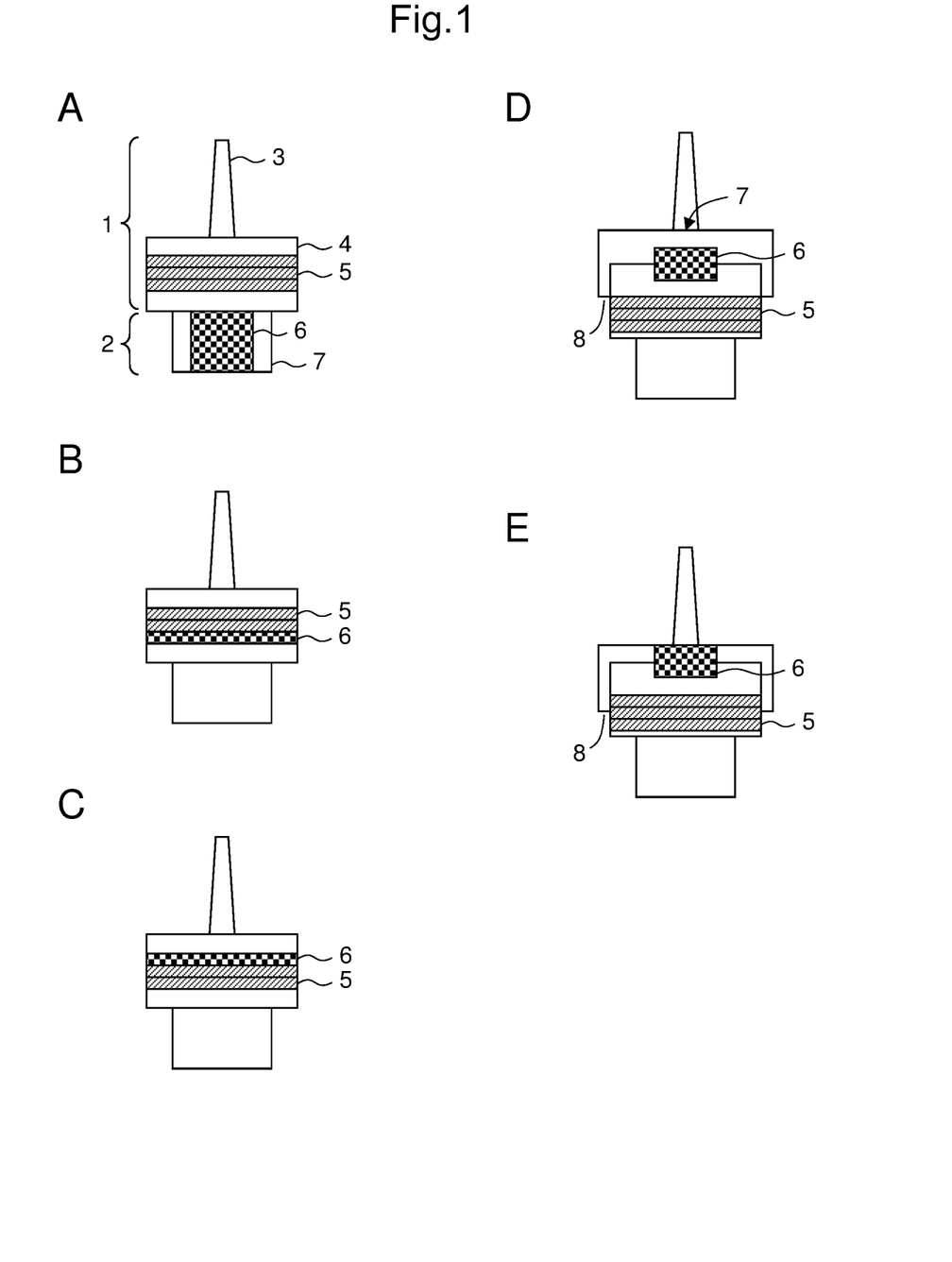
FIG. 1 is a view showing a structure of a specimen adding device for filtration, which is for use in extracting a sugar chain antigen in a filtration step.

FIG. 1 shows an example of a specimen adding device including a filtration means and tartaric acid. However, the specimen adding device of the present invention is not limited to the device shown in FIG. 1. The present specimen adding device includes all types of devices, as long as it is a device capable of accommodating a specimen and adding it to a specimen adding site of an immunochromatographic test piece. In the specimen adding device of FIG. 1, the lower portion is a vessel portion accommodating a specimen, whereas the upper portion is a lid portion (also referred to as a nozzle portion) of the vessel having a specimen adding nozzle. A filter can be set to the lid portion.

In FIG. 1A, a filtration filter used as a filtration means is not contacted with a porous material impregnated with tartaric acid, and they are separated from each other. The porous material impregnated with tartaric acid is located on the side upstream of the filtration filter. In this case, the porous material impregnated with tartaric acid may be immobilized inside of the device, for example, inside of the vessel portion, by a suitable immobilization means. Otherwise, the porous material may not be immobilized but may be just placed inside of the device. Alternatively, the porous material impregnated with tartaric acid may also be added to the device when a nitrous acid treatment is performed. Herein, the term "upstream" is used to mean upstream with regard to the flow of a specimen fluid accommodated in a specimen adding device, when the specimen is added using the device. A portion apart from a specimen adding nozzle in the device is referred to as "upstream," whereas a portion close to the specimen adding nozzle is referred to as "downstream." When the device of FIG. 1A is used, a specimen is placed in a nitrile solution in the device, and the specimen, the nitrite solution, and tartaric acid in the porous material are contacted and mixed with one another according to inverting mixing, so that a nitrous acid treatment is performed on the specimen. Alternatively, it is also possible that a specimen is previously mixed with a nitrous acid solution, and the mixed solution is then added into a vessel in the device, which accommodates tartaric acid, so that the specimen, the nitrile solution, and tartaric acid in the porous material can be contacted and mixed with one another. The obtained mixture is added from a nozzle portion to an immunochromatographic test piece through a filter.

In FIG. 1B, a filtration filter is contacted with a porous material impregnated with tartaric acid, so that they are integrated with each other, and the porous material impregnated with tartaric acid is established on the upstream side of the filter. In this device, the porous material impregnated with tartaric acid can be incorporated as a single layer into a filtration filter consisting of a single layer or multiple layers. In the device shown in FIG. 1B, a nitrite solution is contained in a vessel in the lower portion of the device, and a specimen is first mixed with a nitrous acid solution. When the mixed specimen is added to an immunochromatographic test piece, the specimen is passed through the porous material impregnated with tartaric acid, and at this time, the impregnated tartaric acid is dissolved in the specimen. The specimen is contacted and mixed with the tartaric acid, so that a nitrous acid treatment can be performed on the specimen. The mixture is added from a nozzle portion to the immunochromatographic test piece through a filter.

In FIG. 1C, a filtration filter is contacted with a porous material impregnated with tartaric acid, so that they are integrated with each other, and the porous material impregnated with tartaric acid is established on the downstream side of the filter. In the device shown in FIG. 1C, a nitrite solution is contained in a vessel in the lower portion of the device, and a specimen is first mixed with a nitrous acid solution. When the mixed specimen is added to an immunochromatographic test piece, the mixed specimen is passed through the filter, and then through the porous material impregnated with tartaric acid, and at this time, the impregnated tartaric acid is dissolved in the specimen. The specimen is contacted and mixed with the tartaric acid, so that a nitrous acid treatment can be performed on the specimen. The mixture is added from a nozzle portion to the immunochromatographic test piece through the filter.

In FIG. 1D, a filtration filter used as a filtration means is not contacted with a porous material impregnated with tartaric acid, and they are separated from each other. The porous material impregnated with tartaric acid is located on the downstream side of the filtration filter. In the device of FIG. 1D, a suitable space may be established between a filter and a nozzle, and the porous material impregnated with tartaric acid may be contained in the space. A nitrite solution is contained in a vessel in the lower portion of the device, and the specimen is first mixed with a nitrous acid solution. When the mixed specimen is added to an immunochromatographic test piece, the specimen is passed through the filter and is then contacted and mixed with tartaric acid in the space in which the porous material impregnated with tartaric acid is present, so that a nitrous acid treatment can be performed on the specimen. Since the specimen is temporarily stored in the space, the time at which the specimen is contacted with the porous material impregnated with tartaric acid can be prolonged, so that the sufficient contact of the specimen with the tartaric acid can be achieved. Besides, at this time, it is desirable to establish an air hole communicating the scape portion with the outside of the device. In order to establish such an air hole, the nozzle portion and a portion into which the filter is incorporated may be created separately, as shown in FIG. 1D. When the mixture consisting of the specimen and the tartaric acid is added to the immunochromatographic test piece, the nozzle portion may be pressed against the filter-incorporated portion. Thereby, the air hole is closed, and at the same time, the specimen is added dropwise from the nozzle (FIG. 1E). As such, by incorporating tartaric acid into a filtration means, the contact of a specimen with tartaric acid, the mixing thereof, and filtration can be almost simultaneously carried out by a single step. Moreover, by allowing a specimen adding device to comprise a filtration means into which tartaric acid has been incorporated, the contact of a sample with tartaric acid, the mixing thereof, filtration of impurities, and addition of the mixture of the specimen and the tartaric acid to the immunochromatographic test piece can be almost simultaneously carried out by a single step. The phrase "can be carried out by a single step" is used herein to mean that the contact and mixing of a specimen, a nitrite solution and tartaric acid, and filtration, or the contact and mixing of a specimen, a nitrite solution and tartaric acid, filtration of impurities, and addition of the mixture of a specimen, a nitrite solution and tartaric acid to an immunochromatographic test piece can be continuously carried out. It does not need that these operations are simultaneously carried out. It is to be noted that tartaric acid needs to be incorporated into the filtration means, so that it is not removed before use.

The size of a specimen adding device is not limited. For example, the height thereof is several cm, and the diameter of the thickest portion thereof is approximately several cm. A filter included in the device, a porous material containing tartaric acid, a porous material containing a neutralizing reagent are not limited, either, in terms of size. For example, if it has a round shape, the diameter thereof is approximately several mm to several cm.

The immunochromatographic test piece comprises a support having a detection region, on which an antibody(Antibody 1) that captures a substance to be detected (antigen, etc.) is immobilized, a label region having a movable labeled antibody (Antibody 2), a sample pad to which a specimen is added dropwise, an absorption band that absorbs a developed specimen solution, a backing sheet for adhering these members to one another, and the like.

The immunochromatographic test piece of the present invention may be accommodated in a storing vessel. Such a storing vessel can prevent the degradation of the test piece, which is caused by, for example, ultraviolet ray or moisture contained in the air. Moreover, in the case of treating a specimen or a sample having contamination or infectivity, such a storing vessel can prevent a tester performing an assay from being contaminated or infected with the specimen or the sample. For instance, a resin-made case having a suitable size may be used as a storing vessel, and the device of the present invention may be accommodated in the case. Otherwise, the surface of a test piece, on which an antigen or an antibody has been immobilized, may be coated with a resin-made film or the like (top laminate). There is a case where a storing vessel and a test piece accommodated in the storing vessel are collectively referred to as an immunochromatographic device.

It is to be noted that the number of detection regions and the type of a labeled antibody contained in the label region are not limited to one, and that, by using antibodies corresponding to a plurality of substances to be detected, two or more antigens can be measured on a single test piece.

The support is a material having the property of immobilizing an antibody used to capture a substance to be detected (an antigen), and also, it does not prevent the movement of a liquid in the horizontal direction. Preferably, the support is a porous thin membrane having capillary action, and is a material capable of transporting a liquid and components dispersed in the liquid according to absorption. The material used for the support is not particularly limited, and examples of the material include cellulose, nitrocellulose, cellulose acetate, polyvinylidene difluoride (PVDF), glass fiber, nylon, and polyketone. Among these materials, a thin membrane of nitrocellulose is more preferable. A membrane, on which an antibody is immobilized, is referred to as an "antibody-immobilized membrane."

The label region consists of a porous substrate comprising a labeled antibody, and a commonly used glass fiber, non-woven fabric, and the like can be used herein as a material for the substrate. The substrate is preferably a pad having a thickness of approximately 0.3 mm to 0.6 mm, in order that the substrate is impregnated with a large amount of labeled antibody. A porous substrate that is impregnated with a labeled antibody and is then dried is also referred to as a dry pad.

For the labeling of a labeled antibody, enzymes such as alkaline phosphatase or horse radish peroxidase, metal colloids such as gold colloids, silica particles, cellulose particles, colored polystyrene particles, colored latex particles, etc. are used in many cases. When metal colloidal particles or colored particles such as colored polystyrene particles or colored latex particles are used, color is developed by clumping of these labeling reagents. So, the thus developed color is measured. Particles, on which antibodies are immobilized, are referred to as antibody-immobilized particles.

The detection region indicates a region of the support, on which an antibody used to capture a substance to be detected (an antigen) is immobilized. In the detection region, at least one region, on which an antibody used to capture an antigen is immobilized, is established. The detection region may be comprised in the support, and an antibody may be immobilized on the support.

The sample pad is a site to which a specimen is added dropwise, and is a porous material. The sample pad is a site located most upstream of the immunochromatographic test piece. As a material for the sample pad, a commonly used filter, glass fiber, non-woven fabric, etc. can be used. In order to use a large amount of specimen in immunoassay, the sample pad is preferably a pad having a thickness of approximately 0.3 mm to 1 mm. The specimen also includes a sample prepared using the specimen, such as a sample obtained by suspending the specimen in another solution.

The absorption band is a member for absorbing components, which are supplied to the support and are not associated with the reaction in the detection region. As a material for the absorption band, a highly water-retainable filter, sponge or the like, consisting of a common natural high-molecular-weight compound, synthetic high-molecular-weight compound, etc. can be used. In order to promote the development of a specimen, highly water-absorbable material is preferably used as an absorption band.

The backing sheet is a member used for adhesion and/or immobilization of all of the aforementioned materials, namely, the support, the sample pad, the label region, the absorption band and the like, in which these materials are partially overlapped with one another. The backing sheet is not necessarily required, if these materials are arranged and immobilized with optimal intervals. However, in general, the backing sheet is preferably used for convenience or ease of production or use.

In the immunochromatographic device of the present invention, a control display region (a member) may be further present. The control display region is a site showing that a test is accurately carried out. For example, the control display region is located downstream of the detection region, and emits signals such as coloration, when a specimen sample is passed through the detection region and reaches the control display region. On the control display region, a substance binding to a labeled carrier-bound antibody may be solid-phased, or a reagent such as a pH indicator, the color of which is changed when a specimen reaches, may also be solid-phased. When such a labeled carrier-bound antibody is a mouse monoclonal antibody, an anti-mouse IgG antibody may be used.

The size of an immunochromatographic test piece is not limited. For example, the height thereof is from several cm to more than ten and less than 20 cm, and the width thereof is from approximately several mm to several cm.

In the test piece having the above-described form, the specimen is passed through a porous flow channel formed by connecting a series of members, such as the sample pad, the label region, the support, the detection region, the absorption band and the like, with one another. Accordingly, in the present embodiment, all of these components constitute a specimen moving region. There may also be an embodiment, in which the specimen does not penetrate into various constitutional materials but pass through the interface, depending on the materials or forms of the constitutional materials. However, since the specimen moving region defined in the present description is irrelevant to whether the specimen passes into the material or passes through the interface, the test piece having the aforementioned embodiment is also included in the scope of the present description.

When a sugar chain antigen is extracted and measured using the immunochromatographic test piece and the specimen adding device of the present invention, nitrous acid is generated using a nitrite solution and tartaric acid, and a sugar chain antigen is then extracted. Since the extracted sugar chain antigen solution is acidic, the antigen-antibody reaction is inhibited if the solution is used as is. Thus, the tartaric acid solution needs to be neutralized. For neutralization of the tartaric acid solution, a neutralizing reagent is used. The neutralizing reagent may be added onto the immunochromatographic test piece, or may also be added into the aforementioned specimen adding device. That is to say, the neutralization step may be carried out on the immunochromatographic test piece, or may be carried out in a site separated from the immunochromatographic test piece, such as the inside of the specimen adding device.

The neutralizing reagent may be impregnated into the sample pad, or may be impregnated into the support, or may be impregnated into a porous material that is different from the support, such as a non-woven fabric, and the obtained neutralizing reagent-impregnated porous material may be disposed upstream of the label region.

The region on the immunochromatographic test piece, which is impregnated with the neutralizing reagent, is referred to as a neutralizing reagent region or a basic reagent region.

The immunochromatographic test piece having a neutralizing reagent region has, on the support, a sample pad, a neutralizing reagent region, a label region, a detection region, and an absorption band, from the upstream thereof. Moreover, the sample pad, the neutralizing reagent region, the label region, the detection region, and the absorption band may be contacted or may not be contacted with a region adjacent thereto. Furthermore, the neutralizing reagent region and the label region are not necessarily impregnated into each different porous material, and a plurality of or all of the regions may be impregnated into a single porous material.

When the neutralizing reagent is added to the specimen adding device, the neutralizing reagent is impregnated into a porous material and is then dried before use. Examples of the porous material that can be used herein include a commonly used filter, glass fiber, and non-woven fabric. The dried, neutralizing reagent-impregnated porous material may be added to the specimen adding device, such that the neutralizing reagent-impregnated porous material is located downstream of a porous material impregnated with tartaric acid. For example, in the case of the specimen adding device shown in FIG. 1A, a neutralizing reagent-impregnated porous material may be established in a portion in which a filter is present. Also in the case of the specimen adding device shown in FIG. 1B, a neutralizing reagent-impregnated porous material may be established in a portion in which a filter is present, downstream of a porous material impregnated with tartaric acid. In the case of the specimen adding device shown in FIG. 1C or the specimen adding device shown in FIG. 1D, a porous material impregnated with tartaric acid is established around most downstream of the specimen adding device. It is also possible to establish a neutralizing reagent-impregnated porous material in a nozzle, but preferably, it is established on the immunochromatographic test piece.

The neutralizing reagent used in the present invention is in a solid state at ambient temperature, and does not volatize at a high temperature.

Examples of the neutralizing reagent that is preferably used in the present invention include Tris (tris(hydroxymethyl)aminomethane), sodium hydroxide, dipotassium hydrogen phosphate, trisodium citrate, and a Good's buffer having a buffering ability in the alkaline range.

The amount of the neutralizing reagent used in the present invention, namely, the amount of the neutralizing reagent impregnated into the immunochromatographic test piece is not particularly limited. In general, the neutralizing reagent is used in an amount of approximately 0.01 µg to 1 mg, and preferably approximately 0.1 µg to 0.1 mg, for a porous material, or for a single immunochromatographic test piece. However, it is preferable to select an optimal amount, in which effects can be obtained depending on the type of the used neutralizing reagent, the composition of a specimen suspension, the amount added dropwise, etc.

In order to impregnate a sample pad or a porous material with the neutralizing reagent, the neutralizing reagent may be once dissolved in a solution, the obtained solution may be then applied to the sample pad or the porous material, and thereafter, it may be dried.

Figure 2:
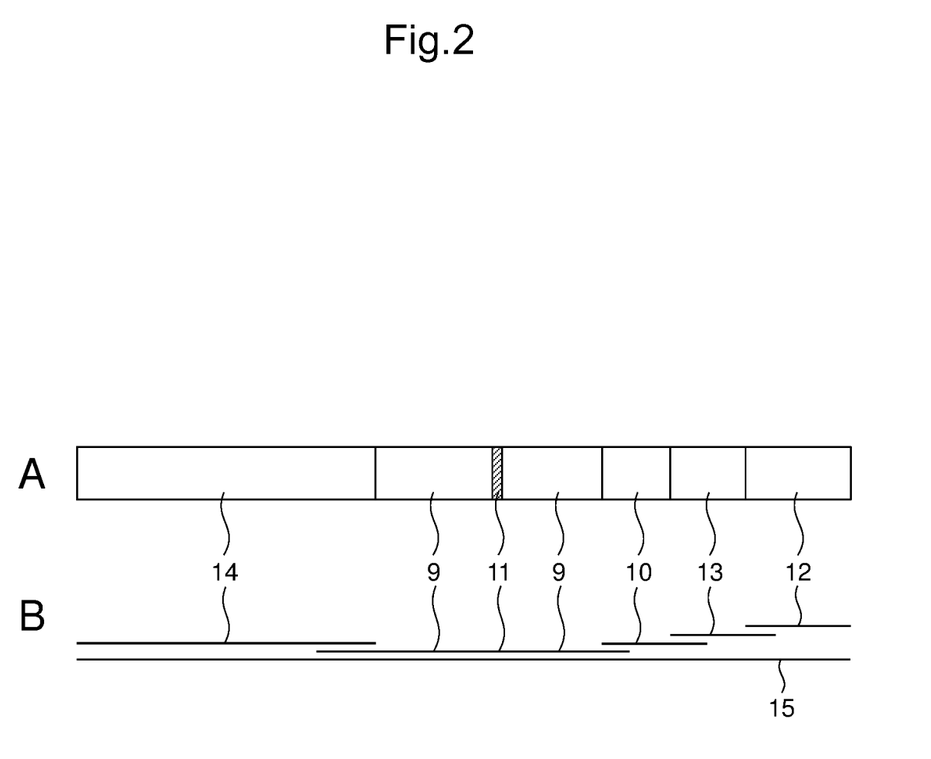
FIG. 2 is a view schematically showing a structure of an immunochromatographic test piece having a neutralizing reagent region (first example).
Figure 3:
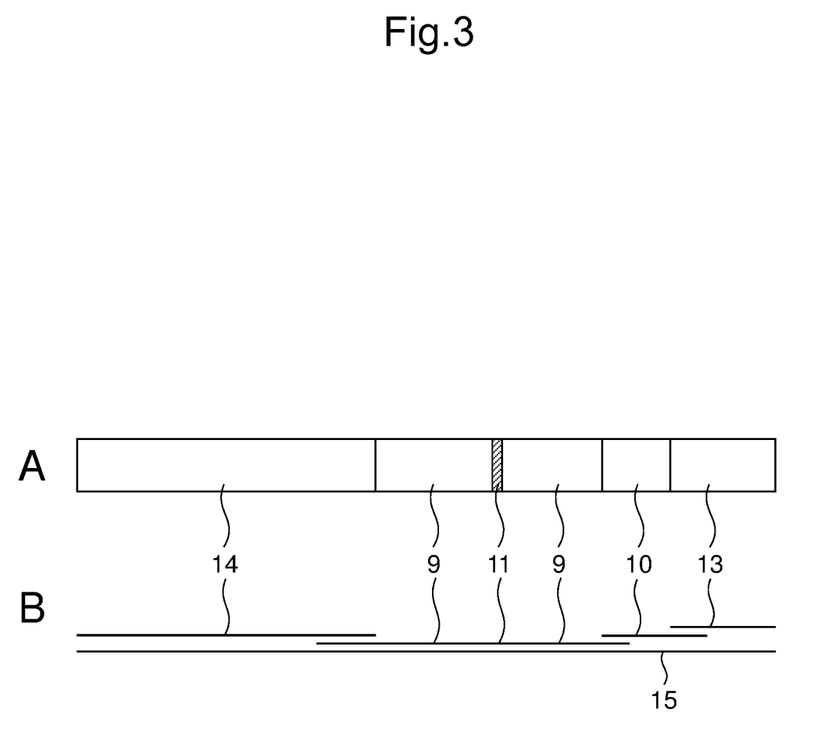
FIG. 3 is a view schematically showing a structure of an immunochromatographic test piece having a neutralizing reagent region (second example).

FIG. 2 and FIG. 3 are views each showing a preferred embodiment of a typical immunochromatographic test piece. The immunochromatographic test piece shown in FIG. 2 is referred to as a first example, and the immunochromatographic test piece shown in FIG. 3 is referred to as a second example. It is to be noted that the immunochromatographic test piece is not limited to those shown in FIG. 2 and FIG. 3. In FIG. 2 and FIG. 3, reference numeral 9 denotes a support, reference numeral 10 denotes a label region, reference numeral 11 denotes a detection region, reference numerals 12 and 13 denote sample pads, reference numeral 14 denotes an absorption band, and reference numeral 15 denotes a backing sheet. Moreover, a top laminate may adhere onto the entire test piece.

FIG. 2A and FIG. 3A are top views, and FIG. 2B and FIG. 3B are cross-sectional views. In the example shown in FIG. 2, a support 9 on which one detection region 11 is formed, an absorption band 14, a label region 10, sample pads 12 and 13, and the like, are laminated on a backing sheet 15 made of resin or the like. As shown in FIG. 3, one end of the absorption band 14 is laminated on one end of the support 9, the other end of the support 9 is laminated on one end of the label region 10, and the other end of the label region 10 is laminated on one end of the sample pad 13. A portion upstream of the sample pad 13 is impregnated with tartaric acid, and a neutralizing reagent region impregnated with a neutralizing reagent is present at a portion downstream of the sample pad, which is somewhat apart from the upstream portion. In the example shown in FIG. 2, the neutralizing reagent region 13 is present upstream of the label region 10, and these are overlapped with each other, so that a flow channel of a continuous lateral flow is formed. In the test piece shown in FIG. 3, the neutralizing reagent region 13 also serves as a sample pad. That is, a neutralizing reagent region is present on the sample pad. A sample pad may further be present upstream of the neutralizing reagent region.

Besides, when a neutralizing reagent is established in the specimen adding device, it is not necessary to establish a neutralizing reagent region on the immunochromatographic test piece.

Using the specimen adding device shown in FIG. 1A or FIG. 1B and the immunochromatographic test piece having a neutralization region shown in FIG. 2, a method of measuring a sugar chain antigen will be described. In the case of using the specimen adding device shown in FIG. 1A, a specimen or a sample prepared using the specimen is contacted and mixed with a nitrite solution, and the specimen is suspended in the nitrite solution, and the suspension is then added to the specimen adding device, so that the reaction is initiated. This time, 5 to 100 µL of a specimen may be mixed with 0.01 to 2 mL of 0.1 M to 8 M nitrite, and the mixture may be then added to the specimen adding device. Examples of the nitrite include sodium nitrite and potassium nitrite. In the case of using the specimen adding device shown in FIG. 1B, a nitrite solution has previously been added into a vessel portion of the specimen adding device, and a specimen is then added into the vessel portion. That is, 0.01 to 2 mL of 0.1 M to 8 M nitrile has previously been added into a vessel portion of the specimen adding device, and 5 to 100 µL of a specimen may be then added into the vessel portion.

When the specimen contained in the specimen adding device is added dropwise onto the sample pad 12 of the immunochromatographic test piece through a nozzle, the specimen is passed through the filter, and at the same time, the specimen is contacted and mixed with tartaric acid impregnated into a porous material. The nitrite contained in the specimen reacts with the tartaric acid, and thereby, free nitrous acid is generated. By the action of such nitrous acid, a sugar chain antigen is extracted from the specimen. A specimen containing the extracted sugar chain antigen is added to the immunochromatographic test piece. When a neutralizing reagent is contained in the specimen adding device, the specimen is neutralized before being added to the immunochromatographic test piece. On the other hand, when a neutralizing agent is contained on the immunochromatographic test piece, the specimen is neutralized on the immunochromatographic test piece.

In the case of using an immunochromatographic test piece comprising a neutralizing reagent region, a specimen containing a sugar chain antigen as a substance to be detected, which is subjected to a sample pad 12, is developed to the sample pad 12 and a neutralizing reagent region 13 according to capillary action, and further, is successively developed to a label region 10, a support 9, and an absorption band 14 in the horizontal direction. The extracted sugar chain antigen is developed and moved, together with an acidic developing solution, to the neutralizing reagent region 13, and the pH of the acidic developing solution containing the sugar chain antigen is neutralized at the neutralizing reagent region 13, so that it is adjusted to the neutral range. As a result, the sugar chain antigen is further developed and moved to the downstream region under neutral conditions. In the label region 10, with the development of a specimen sample, a labeled antibody is released into the liquid, and it is then developed to the support 9. When a sugar chain antigen is present in a specimen sample, the sugar chain antigen is specifically captured by a capturing antibody at a detection region 11 in the support 9, and the sugar chain antigen also has a specific reaction with a labeled antibody to form a complex. Thereby, at the detection region, the sandwiching of the antibody via the sugar chain antigen is achieved, so that a labeled antibody-sugar chain antigen complex can be measured at the detection region 11.

According to the method using an immunochromatographic test piece of the present invention, since the extraction of a sugar chain antigen from a specimen is carried out in a specimen adding device, it is not necessary to previously extract the sugar chain antigen from the specimen before the measurement using the immunochromatographic test piece and the specimen adding device, but the sugar chain antigen in the specimen can be measured by a single step.

In the method of the present invention, a biological sample used as a specimen is not particularly limited. Examples of such a biological sample include body fluid and the like such as serum, plasma, blood, urine, feces, saliva, tissue fluid, spinal fluid or swab, and a diluted product thereof. The specimen adding device used in the method of the present invention includes a filtration means. Hence, pharynx or nasal swab, pharynx or nasal washed solution, nasal aspirate, saliva, rectal swab, feces, fecal suspension, corneal swab, and the like, all of which contain a solid or the like and thus require filtration, are preferably used herein as biological samples.

In the method using an immunochromatographic test piece of the present invention, a substance to be detected as an analyte is a sugar chain antigen, which can be measured by an immunoassay, namely, an assay utilizing an antigen-antibody reaction. An example of the antigen is a polysaccharide that is a sugar chain antigen present on the cell wall of bacteria extracted by a nitrous acid extraction treatment. Protozoa, fungi, bacteria, mycoplasma, rickettsia, chlamydia, virus, and others comprising the aforementioned substance can also be measured. According to the method using an immunochromatographic test piece of the present invention, whether or not a sugar chain antigen derived from protozoa, fungi, bacteria, mycoplasma, rickettsia, chlamydia, virus, etc. is contained in the biological sample of a subject can be confirmed. When such a sugar chain antigen is contained in the biological sample, it can be determined that the subject is affected with infection caused by the protozoa, fungi, bacteria, mycoplasma, rickettsia, chlamydia, virus, etc. For example, group A β-hemolytic streptococcus (*Streptococcus pyogenes*), the presence or absence of infection with *Escherichia coli*, Legionella, Campylobacter, etc. can be detected.

EXAMPLES

Hereinafter, the present invention will be more specifically described in the following examples. However, these examples are not intended to limit the scope of the present invention.

Example 1: Effects Obtained by Conventional Method and Present Method

1. Immobilization of Anti-*Streptococcus pyogenes* (Group A β-Hemolytic Streptococcus) Antibody on Nitrocellulose Membrane A solution obtained by diluting an anti-*Streptococcus pyogenes* antibody with purified water to a concentration of 1.0 mg/mL and an anti-rabbit IgG antibody were prepared. The anti-*Streptococcus pyogenes* antibody was linearly applied to the sample pad side of a nitrocellulose membrane backed with a PET film, and the anti-rabbit IgG antibody was linearly applied to the absorption band side thereof. Thereafter, the nitrocellulose membrane was dried at 45° C. for 30 minutes to obtain an anti-*Streptococcus pyogenes* antibody-immobilized membrane. This membrane is referred to as an "antibody-immobilized membrane" in the present example.

2. Immobilization of Anti-*Streptococcus pyogenes* Antibody on Colored Polystyrene Particles An anti-*Streptococcus pyogenes* antibody was diluted with purified water to a concentration of 1.0 mg/mL, and colored polystyrene particles were then added to the obtained solution to a concentration of 0.1%, followed by stirring. Thereafter, carbodiimide was added to the mixed solution to a concentration of 1%, and the obtained mixture was further stirred. A supernatant was removed from the reaction mixture by a centrifugal operation, and was then re-suspended in 50 mM Tris (pH 9.0) and 3% BSA to obtain a 0.04% anti-*Streptococcus pyogenes* antibody-bound colored polystyrene particle suspension. These particles are referred to as "antibody-immobilized particles" in the present example.

3. Application and Drying of Anti-*Streptococcus pyogenes* Antibody-Bound Colored Polystyrene Particles The antibody-immobilized particle suspension produced in the above 2 was applied in a predetermined amount to a non-woven fabric, and was then dried at 45° C. for 30 minutes. The obtained non-woven fabric is referred to as a "dry pad" in the present example.

4. Production of Neutralizing Reagent (Basic Reagent)-Impregnated Non-Woven Fabric As a neutralizing reagent (basic reagent), 2 M Tris (Trizma Base) was applied in a concentration of 15 μL/cm to a non-woven fabric. Immediately after the application, the non-woven fabric was dried at 45° C. for 1 hour to obtain a neutralizing reagent-impregnated non-woven fabric.

5. Production of Acid Reagent-Impregnated Non-Woven Fabric

As an acid reagent, 1 M hydrochloric acid, 1 M acetic acid, 1 M malonic acid, 1 M malic acid, 1 M maleic acid, 1 M citric acid, or 1 M tartaric acid was applied in an amount of 3.75 μL each to a non-woven fabric. Immediately after the application, the non-woven fabric was dried at 45° C. for 1 hour to obtain an acid reagent-impregnated non-woven fabric.

6. Production of *Streptococcus pyogenes* Test Piece

The antibody-immobilized membrane produced in the above 1, the dry pad produced in the above 3, and the neutralizing reagent (basic reagent)-impregnated non-woven fabric produced in the above 4 were each adhered to other members (a backing sheet and an absorption band), followed by cutting the resultant into a piece with a width of 5 mm, thereby producing a *Streptococcus pyogenes* test piece. In addition, a device having a nozzle, in which the acid reagent-impregnated non-woven fabric produced in the above 5 is incorporated into a sample filtration filter, and a test piece, in which the neutralizing reagent (basic reagent)-impregnated non-woven fabric is used as a sample pad, are referred to as "the present test device" and "the present test piece," respectively. The structure of "the present test device" is as shown in FIG. 1A, and the structure of "the present test piece" is as shown in FIG. 2. A similar test piece was produced using a non-woven fabric to which no reagents were applied, instead of using the acid reagent produced in the above 4 and the neutralizing reagent (basic reagent)-impregnated non-woven fabric produced in the above 5, and the thus produced test piece was used as a conventional example. A nozzle, in which a non-woven fabric to which no reagents are applied is incorporated into a sample filtration filter, is referred to as a "conventional method test nozzle," and a test piece using, as a sample pad, such a non-woven fabric to which no reagents are applied, is referred to as a "conventional method test piece." It is to be noted that the test piece comprises, from a site upstream thereof, a neutralizing reagent (basic reagent)-impregnated non-woven fabric, a dry pad (label region), an antibody-immobilized membrane (detection region), and an absorption band, along the flow of a specimen.

7. Specimen

*Streptococcus pyogenes* was cultured, and the culture solution was then adjusted to cell counts of $1.0 \times 10^7$ CFU/mL and $0.25 \times 10^7$ CFU/mL, using a normal saline.

As a negative specimen, a physiological saline was used.

8. Measurement

20 μL of a specimen was suspended in 180 μL of a sodium nitrite solution (2 M $NaNO_2$), and 75 μL of the suspension was then added dropwise onto the present test piece. On the other hand, as a conventional method, a specimen was suspended in a nitrous acid extract solution in which sodium nitrite was mixed with hydrochloric acid, and 50 μL of a specimen suspension that had been neutralized with a Tris solution was then added dropwise onto a conventional method test piece. Five minutes later, the presence or absence of accumulation of colored polystyrene particles in a predetermined position on which an anti-*Streptococcus pyogenes* antibody had been immobilized, and the degree of accumulation, were judged by visual observation. The linear accumulation was judged as +++, ++, and +, in the order of the accumulation strength. When it was hard to judge the accumulation degree, it was judged as ±, and when no accumulation was observed, it was judged as −.

Moreover, as a comparative example, there was also applied a conventional method, which comprises suspending a specimen in a nitrous acid extract solution, in which sodium nitrile has previously been mixed with acetic acid, and then adding the neutralized specimen dropwise onto a conventional method test piece, through a conventional method test nozzle.

9. Results

TABLE 1

| | Judgment results | | | |
|---|---|---|---|---|
| | Negative specimen | Coloration | $1.0 \times 10^7$ CFU/mL | $0.25 \times 10^7$ CFU/mL |
| Comparative Example | − | − | +++ | ++ |
| Hydrochloric acid | − | − | + | − |
| Acetic acid | − | − | + | − |
| Malonic acid | − | +++ | +++ | ± |
| Malic acid | − | + | +++ | ± |
| Maleic acid | ± | − | +++ | ± |
| Citric acid | + | − | +++ | ++ |
| Tartaric acid | − | − | +++ | ++ |

As shown in Table 1, the detection sensitivity of *Streptococcus pyogenes* was significantly reduced in the case of using hydrochloric acid or acetic acid as an acid reagent, in comparison to the conventional method. This is considered because hydrochloric acid and acetic acid have a volatilizing property, and thus, these acids volatilize in a drying step upon the production of an acid reagent-impregnated non-woven fabric and the applied amount is thereby decreased, and as a result, a nitrous acid extraction treatment cannot be carried out.

On the other hand, malonic acid, malic acid, maleic acid, citric acid, and tartaric acid are each present in a powder state at ambient temperature, and thus these acids do not have volatility. Accordingly, even in a drying step upon the production of an acid reagent-impregnated non-woven fabric, the applied amount is not decreased, and thus, a nitrous acid extraction treatment can be carried out with performance that stands comparison with the conventional method. Hence, the sensitivity was not significantly decreased. Moreover, the measurement could be carried out by a smaller number of operations, in comparison to the conventional method. However, malonic acid or malic acid reacted with nitrous acid, so that the immunochromatographic test piece was colored, and maleic acid and citric acid generated a non-specific reaction. Among these acids, tartaric acid did not cause coloration to the immunochromatographic test piece, and stood comparison with the conventional method, in terms of sensitivity and specificity.

Example 2: Studies Regarding Applied Amount of Acid Reagent

The applied amount of the acid reagent was changed in Example 1, and the test results (Table 2) were comparatively analyzed.

TABLE 2

| Applied amount (μL) | Judgment results | | |
|---|---|---|---|
| | Negative specimen | $1.0 \times 10^7$ CFU/mL | $0.25 \times 10^7$ CFU/mL |
| 7.5 | − | +++ | ++ |
| 5.625 | − | +++ | ++ |
| 3.75 | − | +++ | ++ |
| 1.875 | − | ++ | + |
| 0.9375 | − | + | − |
| 0.4688 | − | ± | − |
| 0.2344 | − | − | − |

As shown in Table 2, when the applied amount was 1.875 μL or less, the sensitivity tended to be decreased. On the other hand, even if the acid reagent was applied in an amount of 3.75 μL or more, the sensitivity did not tend to be significantly increased.

All publications, patents, and patent applications cited in the present description are incorporated herein by reference in their entirety.

REFERENCE SIGNS LIST

1 Lid portion
2 Specimen-accommodating vessel portion
3 Nozzle
4 Nozzle portion
5 Filter (a portion of which may optionally be a porous material impregnated with a neutralizing reagent)
6 Porous material impregnated with tartaric acid
7 Space in which tartaric acid and specimen are temporally stored and mixed with each other
8 Air vent hole
9 Support (including a detection region)
10 Label region
11 Detection region
12 Sample pad
13 Neutralizing reagent region
14 Absorption band
15 Backing sheet

The invention claimed is:

1. A method of measuring a sugar chain antigen using an immunochromatographic test piece, the method comprising:
(i) mixing a specimen with a nitrite solution to form a mixture;
(ii) allowing a solid acid reagent to come into contact with the mixture in a filtration step to extract a sugar chain antigen contained in the specimen;
(iii) adding the mixture to an immunochromatographic test piece, wherein the immunochromatographic test piece comprises a sample pad, a neutralizing reagent (basic reagent)-impregnated non-woven fabric, a label region comprising a dry pad, a detection region comprising an antibody-immobilized membrane, and an absorption band, and
(iv) allowing the mixture to flow through the test piece, thereby measuring the sugar chain antigen,
wherein the filtration step is carried out in a specimen adding device separated from an immunochromatographic test piece, the specimen adding device comprising a vessel portion and a lid portion having a specimen adding nozzle and further comprising (i) a porous material impregnated with tartaric acid and (ii) a filter;
wherein allowing a solid acid reagent to come into contact with the mixture to extract a sugar chain antigen is carried out in the filtration step;
wherein the solid acid reagent is neutralized by the neutralizing reagent (basic reagent)-impregnated non-woven fabric; and
wherein the solid acid reagent is tartaric acid,
wherein the dry pad comprises antibody-immobilized colored polystyrene particles.

2. The method of claim 1, wherein neutralizing the tartaric acid comprises the use of a neutralizing reagent, wherein the neutralizing agent is tris(hydroxymethyl)aminomethane or sodium hydroxide.

3. The method of claim 1, wherein the sugar chain antigen is a sugar chain antigen present on protozoa, fungi, bacteria, *mycoplasma, rickettsia, chlamydia, Streptococcus pyogenes*, or virus.

4. The method of claim 1, wherein the porous material impregnated with tartaric acid is a non-woven fabric.

5. The method of claim 1, wherein the porous material impregnated with tartaric acid was obtained by applying 1M tartaric acid to a non-woven fabric in an amount greater than or equal to 3.75 μL.

6. The method of claim 5, wherein, following applying tartaric acid to the non-woven fabric, the non-woven fabric to which the tartaric acid was applied was dried at about 45° C. for about 1 hour.

* * * * *